United States Patent
Parente Duena et al.

(10) Patent No.: US 7,022,668 B2
(45) Date of Patent: Apr. 4, 2006

(54) USE OF A GLYCOPROTEIN FOR THE TREATMENT AND RE-EPITHELIALISATION OF WOUNDS

(75) Inventors: Antonio Parente Duena, Barcelona (ES); Josep Garces Garces, Barcelona (ES); Jesus Guinea Sanchez, Barcelona (ES); Josep Maria Garcia Anton, Barcelona (ES); Ricardo Casaroli Marano, Barcelona (ES); Manuel Reina Del Pozo, Barcelona (ES); Senen Vilaro Coma, Barcelona (ES)

(73) Assignee: Lipotec S.A., (ES)

( * ) Notice: Subject to any disclaimer, the term of this patent is extended or adjusted under 35 U.S.C. 154(b) by 82 days.

(21) Appl. No.: 10/480,538

(22) PCT Filed: Jun. 7, 2002

(86) PCT No.: PCT/ES02/00281

§ 371 (c)(1),
(2), (4) Date: Jan. 6, 2004

(87) PCT Pub. No.: WO02/102406

PCT Pub. Date: Dec. 27, 2002

(65) Prior Publication Data

US 2004/0242466 A1    Dec. 2, 2004

(30) Foreign Application Priority Data

Jun. 14, 2001 (ES) .................................. 200101383

(51) Int. Cl.
*A61K 38/46* (2006.01)
*A61P 17/12* (2006.01)

(52) U.S. Cl. .......................................... 514/8; 530/395
(58) Field of Classification Search ................ 530/300, 530/322, 350, 395; 514/2, 8, 12
See application file for complete search history.

(56) References Cited

FOREIGN PATENT DOCUMENTS

WO    WO 9842731    10/1998

OTHER PUBLICATIONS de la Maza et al. Assembly Properties of a Glycoprotein Produced by Pseudoalteromonas antarctica, NF3. Journal Of Colloid And Interface Science. 1997, vol. 192, pp. 286–293.*
International Search Report for PCT/ES02/00281, dated Nov. 12, 2002.

* cited by examiner

*Primary Examiner*—Jeffrey Edwin Russel
(74) *Attorney, Agent, or Firm*—Ostrolenk, Faber, Gerb & Soffen, LLP

(57) ABSTRACT

Use of a glycoprotein produced by *Pseudoalteromonas antartica* and consisting of 14% carbohydrates and 86% protein in the preparation of pharmaceutical, veterinary and cosmetic compositions for topical or mucous application in the treatment and re-epithelialization of wounds and in the preparation of cosmetic compositions for treatment of skin, hair or nails.

4 Claims, 1 Drawing Sheet

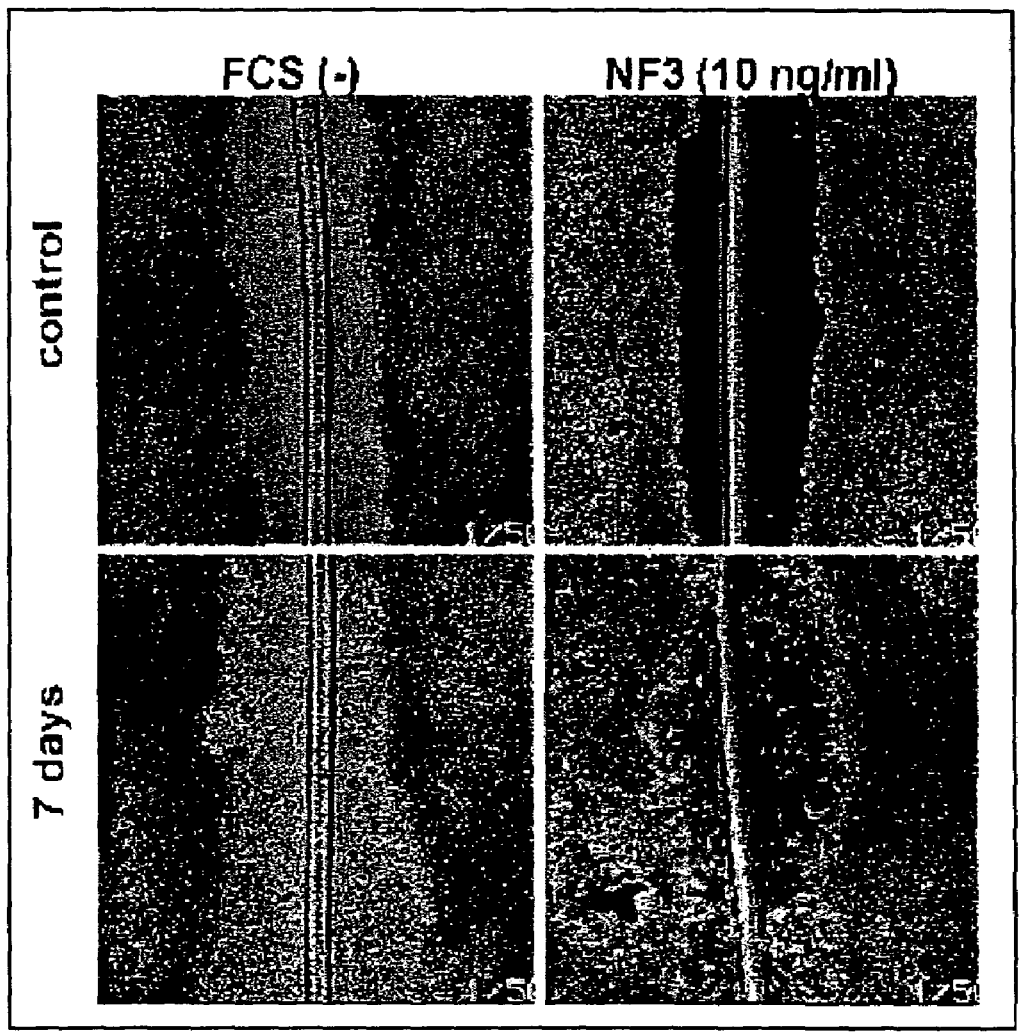
Figure n° 1

USE OF A GLYCOPROTEIN FOR THE TREATMENT AND RE-EPITHELIALISATION OF WOUNDS

FIELD OF THE INVENTION

The present invention relates to the use of a glycoprotein known as Antarticine—NF3 for preparing pharmaceutical, veterinarian and cosmetic compositions for treatment and re-epithelialization of wounds.

DESCRIPTION OF THE RELATED ART

Antarticine—NF3 is a glycoprotein produced by *Pseudoalteromonas antartica*, a Gram-negative bacteria isolated from the Antarctic Ocean. This aerobic heterotropic bacterium has a single polar flagellum and produces a hexapolymeric glycoprotein (Antarticine—NF3) composed of 14% carbohydrate and 86% protein that completely surround it. *Pseudoalteromonas antartica* is perfectly adapted to the low temperatures of the Antarctic environment and withstands high salt concentrations.

Antarticine—NF3 in solution forms regular aggregates by self-assembly. A gradual increase in the concentration of a solution of this glycoprotein causes a gradual reduction of the surface tension of the solution. In addition, Antarticine—NF3 is known for its great affinity to phosphatidylcholine liposome, coating them and protecting them from the permeabilisation effect of surfactants such as SDS, as described in WO98/42731. In addition, Antarticine—NF3 is known for inducing nucleation of ice and preventing the growth of large hexagonal ice crystals. These data suggest that Antarticine—NF3 is responsible for the adaptation of *Pseudoalteromonas antartica* to the environmental conditions of its Antarctic habitat.

Furthermore, keratinocytes are a type of cell found in the epidermis, forming its deepest layer. Keratinocytes generate the outer skin layer (corneal stratum) by multiplication and modification of their structure until forming the layer of mature, keratinocytised cells on the surface of the skin. The speed of healing of wounds is influenced, among other factors, by the rate of proliferation and migration of keratinocytes. Any factor that enhances one of these processes will favour the healing and scarring process for wounds.

SUMMARY OF THE INVENTION

As a result of our investigations we have found that, surprisingly, the soluble glycoprotein from *Pseudoalteromonas antartica* known as Antarticine—NF3, which consists of 14% carbohydrates and 86% protein, selectively improves the adhesion of human dermal fibroblasts and promotes the cellular growth of human epidermal keratinocytes. Thus, Antarticine—NF3 has surprisingly revealed itself as a good agent for improving scar formation in wounds.

Thus, the object of the present invention is the use of Antarticine—NF3 in solutions or acceptable galenical formulations for use in the treatment and re-epithelialization of wounds in the pharmaceutical and veterinary fields, as well as for cosmetic regeneration treatments. The concentrations used of Antarticine—NF3 are between 100 mg/l and 1 fg/ml, and more specifically between 10 mg/ml and 0.1 ng/ml.

BRIEF DESCRIPTION OF THE DRAWING

FIG. 1 shows regeneration of a HEK cell after 7 days of treatment with a composition according to the present invention.

DETAILED DESCRIPTION OF THE INVENTION

As a complement of the description being made and in order to aid a better understanding of the characteristics of the invention, a few examples are provided below for purposes of illustration only and in a non-limiting sense. This invention should not be considered as limited by the realizations described.

EXAMPLE 1

In Vitro Cytotoxicity

Experiments were carried out with the WST-1 test, which measures the activity of mitochondrial dehydrogenases in a non-radioactive calorimeter test using formazan salts. Different concentrations of glycoprotein were tested (between 1 mg/ml and 0.01 µg/ml). NaCl 0.01M was used as a negative control and SDS 0.02% was used as a positive control.

The results obtained are shown in the following table:

|  | Concentration tested | Result on HDF | Result on HEK |
|---|---|---|---|
| Control |  | 0.46 | 0.92 |
| Negative control (NaCl) | 0.01 M | 0.43 | 0.7 |
| Positive control (SDS) | 0.02% | 0.17 | 0.2 |
|  | 1 fg | — | 0.78 |
|  | 0.1 pg | — | 0.92 |
|  | 0.0 ng1 | 0.44 | 0.92 |
|  | 1 ng | 0.43 | 1.02 |
|  | 0.1 µg | 0.41 | 0.97 |
|  | 10 µg | 0.42 | 0.8 |
|  | 1 mg | 0.44 | 0.81 |

As can be seen in the above table, the cytotoxicity tests revealed that Antarticine—NF3 does not show toxicity in human epidermal keratinocytes (HEK), nor in human dermal fibroblasts (HDF).

EXAMPLE 2

Effect on Cellular Adhesion

Cellular adhesion tests in vitro revealed that Antarticine—NF3 has a specific effect on the adhesion of HDF. HDF cells showed a significant growth in cellular adhesion when growing on substrates coated with 1 mg/ml of Antarticine—NF3 after 2 and 5 hours of culture.

The results obtained for HDF are shown in the following table:

|  | Concentration tested | Time 2 hours | Time 5 hours |
|---|---|---|---|
| Control |  | 0.1 | 0.13 |
| Glycoprotein | 0.001 mg/ml | 0.11 | 0.24 |
|  | 1 mg/ml | 0.24 | 0.28 |

The results obtained for HEK are shown in the following table:

| | Concentration tested | Time 2 hours | Time 5 hours |
|---|---|---|---|
| Control | | 0.09 | 0.15 |
| Glycoprotein | 0.001 mg/ml | 0.11 | 0.17 |
| | 1 mg/ml | 0.15 | 0.19 |

As may be seen, in similar culture conditions the effect seen on HEK is not statistically significant.

EXAMPLE 3

Effect on Cell Growth

Experiments on in vitro cell growth conducted with the crystal violet elutionmethod revealed that Antarticine—NF3 at different concentrations, in the presence or absence of a minimal amount of foetal cow serum (2% FCS) stimulates the growth of HEK cells, as shown in the following table:

| | Concentration tested | Time 0 hours | Time 24 hours | Time 48 hours |
|---|---|---|---|---|
| Control | | 0.2 | 0.16 | 0.58 |
| Glycoprotein | 10 µg/mL | | 0.15 | 0.78 |
| | 0.1 µg/mL | | 0.16 | 0.77 |
| | 0.001 µg/mL | | 0.18 | 0.77 |

While similar experiments conducted with HDF cells did not show relevant results, as shown on the following table:

| | Concentration tested | Time 0 hours | Time 24 hours | Time 48 hours |
|---|---|---|---|---|
| Control | | 0.21 | 0.16 | 0.25 |
| Glycoprotein | 10 µg/mL | | 0.175 | 0.26 |
| | 0.1 µg/mL | | 0.17 | 0.248 |
| | 0.001 µg/mL | | 0.175 | 0.249 |

EXAMPLE 4

Effect on In Vitro Wound Regeneration

Experiments for regeneration of wounds in vitro were conducted in cultures of differentiated HEK cells, in the presence and absence of FCS. The duration of the tests was seven days.

Concentrations of Antarticine—NF3 above 0.1 ng/ml showed a positive effect on wound regeneration when compared to control cultures; this effect of Antarticine—NF3 on wound regeneration in vitro can be seen in FIG. 1 for a concentration of 0.1 µg/mL.

The invention claimed is:

1. A method of treating or re-epithelializing wounds comprising administering to said wounds a pharmaceutically effective amount of a glycoprotein produced by *Pseudoalteromonas antartica* which consists of 14% carbohydrates and 86% protein.

2. The method of claim 1, wherein said glycoprotein is administered topically or on the mucous.

3. The method of claim 1, wherein said glycoprotein is present in a composition in a concentration between about 100 mg/ml to about 1 fg/ml.

4. The method of claim 1, wherein said glycoprotein is present in a composition in a concentration between about 10 mg/ml and about 0.1 ng/ml.

* * * * *